(12) United States Patent
Bublewitz et al.

(10) Patent No.: US 6,599,974 B1
(45) Date of Patent: Jul. 29, 2003

(54) IMPRESSION MATERIAL

(75) Inventors: Alexander Bublewitz, Herborn (DE); Jens-Peter Reber, Herborn (DE); Rainer Hahn, Tübingen (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 0 days.

(21) Appl. No.: 09/831,348

(22) PCT Filed: Nov. 11, 1999

(86) PCT No.: PCT/EP99/08663

§ 371 (c)(1),
(2), (4) Date: Aug. 13, 2001

(87) PCT Pub. No.: WO00/27342

PCT Pub. Date: May 18, 2000

(30) Foreign Application Priority Data

Nov. 11, 1998 (DE) .......................................... 198 52 056

(51) Int. Cl.[7] .............................................. C08L 83/05

(52) U.S. Cl. ........................ 524/588; 524/493; 524/543; 524/612; 524/430; 524/436; 524/435; 528/31; 528/32; 528/901; 528/12; 528/15; 528/19; 528/41; 556/444; 525/478; 106/38.2

(58) Field of Search ................................. 524/493, 588, 524/543, 612, 430, 436, 435; 528/31, 32, 901, 12, 15, 19, 41; 556/444; 525/478; 106/38.2

(56) References Cited

U.S. PATENT DOCUMENTS 5,132,343 A * 7/1992 Zwecker et al.
5,955,530 A * 9/1999 Inoue et al.

FOREIGN PATENT DOCUMENTS

| DE | 197 11 314 A1 | 9/1998 |
|---|---|---|
| EP | 0 522 341 A1 | 1/1993 |
| EP | 0 891 763 A2 | 1/1999 |
| WO | WO 97/32536 | 9/1997 |
| WO | WO 98/26748 | 6/1998 |
| WO | 98 52491 | * 11/1998 |

* cited by examiner

Primary Examiner—Robert Dawson
Assistant Examiner—Kuo-Liang Peng
(74) Attorney, Agent, or Firm—Jacobson Holman PLLC

(57) ABSTRACT

An impression material for the use with an impression spoon in patients, wherein the impression material comprises curable components and at least one first filler, characterized in that said at least first filler has a BET surface of from 20 to 50 $m^2/g$, preferably from 30 to 40 $m^2/g$, whereby the impression material attains a low thixotropy and a viscosity of from 1 to 350 Pas.

38 Claims, No Drawings

IMPRESSION MATERIAL

Subject matter of the present invention is an impression material for use with an impression spoon.

WO-A-97/32536 and WO-A-98/52491 describe an impression spoon and an impression material for said impression spoon.

There, the impression material is fed from the rear ends of the impression spoon into the mold cavity confined and sealed between the impression spoon and the jaw and drawn through the groove of the mold to the front end of the impression spoon under the influence of reduced pressure. An introduction of deflector elements in the form of skeleton foams results in a flow component of the impression material parallel to the tooth center promoting the complete impression of undercut and deeper areas.

Using such impression spoons, one obtains highly precise impressions which—as compared to impressions obtained by conventional impression techniques—do not contain any trapped liquids (sulcus liquid, blood) or air bubbles and which do not have any defective wetting, distortions, or elastic recovery of shape after the deformation of the plastic impression material under pressure.

The low-viscous impression materials used in the conventional impression techniques are not or only restrictedly usable with the new impression spoon due to the kinetic and rheological properties thereof.

The impression materials usually used in the conventional impression techniques consist of a multicomponent system:

α) di- and polyalkenylsiloxanes;

β) polyhydrogensiloxanes;

γ) a precious metal catalyst of the 8th side group of the periodic system;

δ) reinforcing fillers;

ε) non-reinforcing fillers.

The technical problem forming the basis of the invention is the provision of an impression compound which can be used in the novel impression spoons according to WO-A-97/32536 and WO-A-98/52491. Another problem is the provision of a formulation which does not sedimentate and separate during storage, the rheological properties of which remain almost unchanged and which results in a cured impression material having mechanical properties which correspond to the features of DIN 24823 (ISO 4823) as well as the required tear resistance and tear propagation resistance.

Said problem is solved by an impression material for use with an impression spoon, wherein the impression material comprises curable components and at least one first filler, characterized in that said at least one filler has a BET surface of from 20 to 50 $m^2/g$, preferably from 30 to 40 $m^2/g$, whereby the impression material becomes slightly thixotropic and attaining a viscosity of from 1 to 350 Pas.

The impression material of the invention is advantageous in that it meets the demands made on the use thereof in the novel impression spoon, in particular the demands made on the impression material with regard to viscosity, reaction kinetics, elastic properties and thixotropy during the flow of the material through the impression spoon. These are in particular:

a) Viscosity

The impression materials of the invention used in the novel impression spoon according to WO-A-97/32536 and WO-A-98/52491 ensure a very good flow behavior which results in an optimal impression. Studies have revealed that the impression results of said novel impression technique are the better the lower the mixed viscosity of the employed impression material is.

Preferably, low-viscous formulations having a mixed viscosity in the range of from 1 to 40 Pas are employed; especially preferred are mixed viscosities of from 1 to 10 Pas.

Low-viscous formulations in this viscosity range have been known in the art (see table 3).

The tooth impression materials having the lowest viscosity (DIN 24823, ISO 4823) obtainable on the market have a mixed viscosity of from 27 to 1100 Pas. The mixed viscosities of the impression materials having the lowest viscosity (Permadyne Garant 2:1, Provil L Panasil contact plus, and Lastic Xtra superfine) exceed the ideal viscosity range of from 1 to 10 Pas. Therefore, said materials used for the conventional impression techniques such as the correction and sandwich impressions have only unsatisfactory impression results in this novel impression technique.

b) Elastic Properties During the Flow Through the Impression Spoon (Reaction Kinetics)

In the novel impression technique according to WO-A-97/32536 and WO-A-98/52491 the impression spoon is filled from the rear to the front. An important criterion is that the mixed viscosity of the inventive impression material during the flow through the impression spoon has to remain almost constant, i.e., no or only very weak elastic properties by chemical crosslinking may be generated. Also here, the marketable products used for the conventional impression techniques (Aquasil LV, Xantopren XL, Coltene President light) have drawbacks. These products are disadvantageous in that they crosslink too fast during the flow through the impression spoon according to WO-A-97/32536 and WO-A-98/52491 and thus generate elastic properties already during the flow through the impression spoon.

When employing the conventional impression materials as such in the novel impression spoon, also this kinetic effect results in unsatisfactory impression results.

c) Thixotropy

The impression materials of the invention employed in the novel impression spoon according to WO-A-97/32536 and WO-A-98/52491 ensure that the thixotropy is as low as possible, which considerably contributes to an optimum impression. Studies have revealed that the impression results obtained with the use of this novel impression technique are the better the lower the thixotropy of the employed impression material is. Usually, the impression materials employed in accordance with prior art have thixotropic properties (e.g., Panasil contact plus, thixotropic index: 1.7).

In the novel impression technique, said impression materials revealed only unsatisfactory impression results since said impression materials form flow trails in the shadow area of the flow direction when flowing through the impression spoon from the rear to the front around the teeth.

In addition to the above-mentioned properties, the inventive impression material for the novel impression technique meets further demands which will be explained below:

Mechanical Properties of the Cured Impression Material

The inventive impression materials for the novel impression technique according to WO-A-97/32536 and WO-A-98/52491 meet the demands of type 3 of DIN 24823 and ISO 4823, resp., with regard to the compression set in the range of from 2 to 20% and the recovery of shape after the compression in the range of from 96.5 to 100%, a linear dimensional change (polymerization shrinkage) in the range of from 0 to 1.5%, and an accuracy of reproduction of 0.02 mm.

The Shore hardness (DIN 53505, ISO 868) of the cured impression material of the invention is between a Shore A of from 30 to 50, preferably from 35 to 45, which is advantageous for the novel impression technique according to WO-A-97/32536 and WO-A-98/52491.

Some impression materials in accordance with prior art used for the conventional impression techniques have Shore A hardnesses of >50. (Aquasil LV: Shore A of 58, Coltene, President light body: a Shore A of 59). High Shore A hardnesses render the removal of the cured impression material from the mouth more difficult.

In the novel impression technique according to WO-A97/32536 and WO-A-98/52491, inventive impression materials having minimum tear resistance and tear propagation resistance values (according to DIN/EN 53504 and DIN 53515) in the cured state of from 150 N/cm$^2$ to 250 N/cm$^2$ and 0.5 to 2.5 N/mm, resp., are employed.

In the novel impression technique according to WO-A97/32536 and WO-A-98/52491 the teeth are reproduced faithfully in every detail, Gaps between the teeth and fissures between crowns and tooth stamps are completely filled with impression material. After the curing of the impression material, the tear resistance and tear propagation resistance values have to be so high that the impression can be removed from the mouth and the impression spoon without being destroyed. On the other side, the tear resistance and tear propagation resistance values must not be excessive in order to avoid excessive stresses on the patient's attachment apparatus during the removal of the cured impression material from the mouth.

The Impression Materials for the Novel Impression Technique

As mentioned above, the novel impression technique according to WO-A-97/32536 and WO-A-98/52491 makes particularly high demands on the rheological properties. Surprisingly, the impression material of the invention meets these demands.

Hereinafter, preferred embodiments of the impression material of the invention are described.

A suitable impression material for the novel impression technique has a very low mixed viscosity (between 1 and 10 Pas) and no or only very low thixotropic properties (thixotropic index $\leq 1.2$, in particular $\leq 1.1$).

A mixed viscosity between 1 and 10 Pas of the multi-component material, usually a two-component material, means that the viscosities of the single components are below or equal to 1 to 10 Pas and the thixotropies are below or equal to 1.2, in particular 1.1.

Contrary to the single components of impression materials according to prior art having no or a low viscosity in the above mentioned viscosity range of from 1 to 10 Pas, the impression materials of the invention are not prone to a sedimentation of the fillers and a separation of the polymers or softeners in the storage time.

The storage stability of dental impression materials in primary packages should be at least from 18 months to 36 months. In this time said separation and sedimentation phenomena may not occur since the features of quality of the impression material will suffer otherwise. Further, the adjusted rheological properties may only vary within narrow tolerances in the storage time in order to ensure the required flow properties.

Above all, the poststiffening phenomenon frequently occurring in the practice, i.e., the increase of viscosity and thixotropy in the storage time, should be avoided as far as possible.

A certain, easily reducable thixotropy of the single components of the inventive impression material is acceptable and even advantageous for the storage stability with regard to sedimentation and separation since the filler particles are kept in suspension in thixotropic single components.

The requirement for this is that the thixotropy of the single components affects the thixotropy of the mixed impression mass since the flowability of the impression material in the novel impression spoon will be impaired otherwise.

The impression material according to the invention meets the following demands:

The mixed viscosity is between 1 and 350 Pas, the impression material does not or nearly not have thixotropic properties, the rheological properties remain nearly constant in the storage time, and no sedimentation or separation occurs in the storage time.

Further, the mechanical properties of the cured impression material concerning the tear resistance, tear propagation resistance, Shore A hardness, and the requirements of DIN EN 24823 (ISO 4823) meet the demands stated above.

In a preferred embodiment, the mixed viscosity is from 1 to 40 Pas, in particular preferably from 1 to 10 Pas. In order to realize the required mixed viscosities of from 1 to 350 Pa, in particular from 1 to 40 Pas, preferably from 1 to 10 Pas, the single viscosities of the single components of a two-component impression material have to be within the mentioned limits. Moreover, it is also possible that one single component has a very high viscosity and the other one a very low viscosity. According to the invention, the mixture must have a viscosity of from 1 to 350 Pas, in particular from 1 to 40 Pas, preferably from 1 to 10 Pas in this case.

According to the invention, a low-viscous, non-thixotropic impression material which has a mixed viscosity within the above-mentioned limits and a thixotropic index of from 1.0 to 1.2 and rheological properties remaining unchanged during the storing, which does not sedimentate in the storage time and has mechanical properties after curing meeting the features required according to ISO 4823 and the required tear resistance and tear propagation resistance can be produced.

Preferably, this can be achieved by using a first inorganic filler having a BET surface between 20 and 50 m$^2$/g, which may be hydrophobized, in the impression material of the invention.

Especially preferred is a combination of said inorganic filler with a reinforcing inorganic filler having a BET surface which is greater than that of the first filler and which is preferably between 50 to 700 m$^2$/g, in particular from 110 to 170 m$^2$/g.

Another subject matter of the present invention is a filler combination of a first and a second filler, wherein the first inorganic filler has a BET surface of from 20 to 50 m$^2$/g and the second filler is an inorganic reinforcing filler having a greater BET surface than the surface of the chosen first filler. Preferably, the second filler has a BET surface of from 50 to 700 m/g, in particular from 110 to 170 m$^2$/g.

In particular, the inorganic filler of the invention has the following features:

The density is of from 2.0 to 2.2 g/cm$^3$, the BET surface is of from 20 to 50 m$^2$/g, in particular from 30 to 40 m$^2$/g, e.g., about 35 m$^2$/g. Due to the production-engineering conditions, the BET surface has a fluctuation range, the mean value of which is here Taken as a base. Typically, the fluctuation range is of from ±5 to 15 m$^2$/g. The dibutyl phthalate adsorption according to DIN 53601 is from 140 to 180 g/100 g. The oil adsorption according to DIN ISO 7875 is from 35 to 60 g/100. The mean particle size is from 0.5 to 20 μm.

Preferably, the inorganic filler of the invention is a wet-precipitated silicic acid or a naturally occurring silicic acid. As compared to pyrogenic silicic acid, said acids may have a relatively high water content of from 2 to 8%.

The inorganic fillers of the invention consist of from 80 to 100% of silicon dioxide. Further, they may comprise other metal oxides such as aluminium oxide, calcium oxide, sodium oxide, potassium oxide, iron oxide, and titanium oxide. Especially preferred as metal oxides in addition to silicon dioxide are calcium oxide, sodium oxide, potassium oxide, and aluminium oxide.

In particular, the hydrophobized silicic acid which—according to the invention—has to be employed in combination with the inventive inorganic reinforcing filler having a BET surface of from 20 to 50 m$^2$/g has the following characteristics:

The density is between 2.0 and 2.2 g/cm$^3$, the BET surface is from 110 to 170 m$^2$/g, in particular between 130 and 150 m$^2$/g.

The primary particle size is between 5 and 30 nm.

The hydrophobized, highly dispersed silicic acid is preferably prepared by a flame hydrolysis of silicon tetrachloride.

Said highly dispersed silicic acid is a hydrophobized, highly dispersed silicic acid being a synthetic, X-ray amorphous silicon dioxide.

The hydrophobized, highly dispersed silicic acid is preferably surface-treated with trimethylsilyl groups. The degree of hydrophobicity is characterized by a carbon content of from 1 to 6% and preferably between 2 and 3%.

In the production, said hydrophobized silicic acid is preferably subjected to an additional refining step, an intense mechanical treatment by a pan mill or a ball mill.

The impression material of the invention on the basis of addition crosslinking silicones for the impression technique employing the novel impression spoon preferably consists of the following ingredients:

α) di- and polyalkenylsiloxanes;
β) polyhydrogensiloxanes;
γ) a precious metal catalyst of the 8th side group of the periodic system;
δ) optionally a reinforcing filler in the form of a hydrophobized, highly dispersed silicic acid having a BET surface of from 110 to 170 m$^2$/g;
ε) an inorganic filler having a BET surface of from 20 to 50 m$^2$/g which may be hydrophobized, and optionally auxiliary agents such as softeners, surfactants, dyes, and polyether-siloxane copolymers which optionally contain vinyl or SiH groups.

Usually, the ingredients are divided into two separated components:

For example:
A component α)+γ)+ε)+δ)
B component β)+ε)+optionally α).

An Especially Preferred Impression Material of the Invention Has the Following Composition of Ingredients:

α) α,ω-vinyl-terminated polydimethylsiloxanes in a percentage range of from 40 to 80%, in particular from 50 to 70%;
β) polyhydrogenpolydimethylsiloxanes having at least 2 SiH groups or a SiH contents of from 0.1 to 15 mmol/g in a percentage range of from 2 to 40%, in particular from 10 to 30%;
γ) hydrosilylation catalysts, salts, complex and colloidal forms of the transition metals of the 8th side group of the periodic system, preferably the platinum, palladium, and rhodium metals, in particular platinum catalysts prepared from, e.g., hexachloroplatinic acid, or from platinum salts (Karstedt catalysts) in a percentage range of from 0.0001 to 0.1%, in particular from 0.0005 to 0.1%, based on the pure metal;
δ) optionally a reinforcing filler in the form of hydrophobized, highly dispersed silicic acid having a BET surface of from 130 to 150 m$^2$/g in a weight range of from 0 to 30%;
ε) an inorganic filler having a BET surface of from 30 to 40 m$^2$/g which may be hydrophobized in a percentage range of from 10 to 50%, in particular from 20 to 30%.

It has been known that the platinum catalyst is irreversibly destroyed already in the presence of low concentrations of acids, bases, or water. This becomes apparent during a longer storage under mom temperature conditions after about 6 months or during a temperature stress test, e.g., at 60° C., already after 1 to 2 weeks in that the crosslinking reaction of the two-component mixture is strongly retarded or fails completely.

This effect cannot be tolerated for a dental impression material. Acids, water, and, above all, bases initiate the cleavage of hydrogen from hydrogenpolysiloxanes.

This results on the one hand in a swelling of the primary package due to the development of hydrogen gas and on the other hand in a delayed crosslinking reaction and a weakening of the cured silicone rubber during the addition reaction of the two-component material due to missing SiH functionalities.

Surprisingly, according to the invention also inorganic fillers having a BET surface of from 20 to 50 m$^2$/g having a high water content of up to 10% and/or a very high pH value of up to 11 may be used.

After the drying of said fillers, formulations of addition crosslinking silicones with said fillers are stable.

The A component of a two component impression material containing the platinum catalyst does not exhibit any impairment of the setting kinetics in the storage time of up to 36 months. In the B component containing polyhydrogensiloxanes no development of hydrogen can be detected in this storage time.

The impression material of the invention (see examples 27, 33) is distinguished by a very good flowability. The mixed viscosity is adjustable between 1 and 40 Pas depending on the chain length of the employed silicone polymers; especially good impression results may be obtained with mixed viscosities between 1 and 10 Pas.

In the mixed state the impression material has no relevant thixotropic properties. The mixed viscosity and the non-relevant thixotropic properties remain nearly unchanged in the storage time.

The use of the inorganic filler of the invention prevents the sedimentation of the filler and the separation of the silicone polymers in the storage time of up to 36 months at room temperature.

With the impression material of the invention, the setting characteristics of the impression material may be adjusted within wide ranges in a matter known as such, e.g., by employing and selecting inhibitors.

The processing time, i.e., the time required by the impression material to flow through the novel impression spoon, is between 20 and 120 s, preferably between 25 and 60 s.

After the complete filling of the novel impression spoon within the mouth of the patient the impression material cures within 2.0 to 10.0 min. Curing times between 2.0 and 4.0 min are especially preferred since they reduce the expenditures in time of the attending dentist and the stress of the patient.

With respect to the impression materials in accordance with prior art, the impression material of the invention is distinguished in that the mixed viscosity thereof during the flow through the impression spoon remains nearly constant, i.e., the reaction kinetics is adjusted such that no or only very weak elastic properties by chemical crosslinking are created in the flow time. After termination of the flow stadium, the impression material of the invention preferably cures very fast (snap effect). The mechanical properties of the impression material of the invention meet the requirements of DIN EN 24823 (ISO 4823). The recovery of shape after deformation is between 96.5 and 100.0%, in particular between 99.0 and 100%. The compression set is between 2.0 and 20.0%, in particular between 5.0 and 15.0.

The Shore A hardness of the impression material of the invention is between 30 and 50, in particular between 35 and 45. The tear resistance and the tear propagation resistance of the impression material of the invention are between 150 and 250 N/cm$^2$ and between 0.5 and 2.5 N/mm, resp. After the curing of the impression material, these mechanical properties of the impression material of the invention ensure a non-destructive removal of the impression spoon from the mouth of the patient and a removal of the impression from the impression spoon. On the other side, the mechanical properties are designed such that any damage of the patient's attachment apparatus during the removal from the mouth is excluded.

In the following, the individual components of the impression materials of the invention will be investigated in order to illustrate the significance of the blends and the optimization thereof.

Comparative Examples a) Formulations comprised of a vinylsiloxane, a SiH siloxane, and a platinum catalyst which do not contain any filler; in the formulations thereof, the chain lengths of the employed silicone polymers within the individual components may vary such that the mixed viscosity is within the above-mentioned limits, especially preferred from 1 to 10 Pas. The mixture of such formulations has very good flow properties. There is no thixotropy.

However, the mechanical properties of the cured impression material are completely insufficient independent of the degree of crosslinking (see comparative example 3).

In all of the following examples, the maximum possible concentration of reinforcing or non-reinforcing fillers being adjustable at the upper limit of the mixed viscosity was added.

In all cases, silicic acids and fillers hydrophobized with trimethylsilyl groups were employed in order to obtain a maximum compatibility with the silicone matrix, b) Formulations comprised of a vinylsiloxane, a SiH siloxane, a Pt catalyst, and reinforcing fillers.

Here, the following becomes apparent:

With low and high concentrations of the highly-dispersed silicic acid (reinforcing filler) the required mixed viscosities as described under a) are attained, however, although the mechanical properties as compared to a) are substantially improved, they are not satisfactorily met (see comparative examples 6 and 24).

c) Formulations comprised of a vinylsiloxane, a SiH siloxane, a Pt catalyst, and non-reinforcing fillers.

The desired mixed viscosities are attainable even with high concentrations of non-reinforcing fillers, however, the mechanical properties are not suited for an application in the novel impression technique. Moreover, the employed non-reinforcing fillers sedimentate in the storage test (see comparative examples 7, 8, 9).

d) Formulations comprised of a vinylsiloxane, a SiH siloxane, a Pt catalyst, and a combination of a reinforcing filler and a non-reinforcing filler.

d1) In a first borderline case of possible combinations, a high concentration of a reinforcing filler and a low concentration of a non-reinforcing filler are used.

The required mixed viscosity is adjustable, however, the mechanical properties of the cured impression material are also insufficient. Moreover, already in this case a tendency of a sedimentation of the non-reinforcing fillers in the storage test occurs (see comparative examples 10, 11, and 12).

d2) In a second borderline case, a low concentration of a reinforcing filler is combined with a high concentration of a non-reinforcing filler.

The required mixed viscosity is adjustable, however, the mechanical properties of the cured impression material are not suitable for the use with the novel impression technique. Moreover, a heavy, not acceptable sedimentation occurs in the storage test (see comparative examples 16, 17, 18, 9, 20, and 21).

d3) With the use of medium concentrations of non-reinforcing and reinforcing fillers, the required mixed viscosity may be adjusted as well.

In the storage time the mixed viscosity of the impression materials increases such that the flow properties and thus the impression result are not ensured during storage.

The cured impression material has moderate but still insufficient mechanical properties.

In the storage test, a medium sedimentation tendency is noted (see comparative examples 13, 14, and 15).

The above-mentioned embodiments reveal that none of the formulations being within the mixed viscosity range of the impression material of the invention, preferably between 1 and 10 Pas, meet the primary requirements with regard to the mechanical properties of the cured impression material and the storage stability regarding poststiffening, separation, and sedimentation.

Hence, the positive properties resulting as such from the increase of the concentrations of reinforcing and non-reinforcing fillers result in rheological drawbacks; i.e., by increasing the concentration of the reinforcing fillers the viscosity of the individual component increases drastically. In addition, the tendency of poststiffening in the storage time increases. With non-reinforcing fillers, a sedimentation of the fillers in the storage time and a separation of the polymers occurs. In addition, the tear resistance and the tear propagation resistance are impaired.

It is especially referred to the tables following the examples which summarize the results of the examples.

The invention is described in more detail in the following examples:

EXAMPLE 1

Comparative Example

An A component of an impression material which does not contain any filler.

99 parts of a vinyl-terminated polydimethylsiloxane having a viscosity of from 7.0 Pas at 20° C. are homogeneously mixed with 1 part of a platinum catalyst of the Karstedt type having a pure platinum content of 1% under vacuum in a vacuum mixer for 15 min.

One obtains a low-viscous paste having a viscosity of 6.4 Pas which does not have any thixotropy (thixotropic index: 1.0).

The rheological properties of the paste do not change, and naturally the paste does not feature any sedimentation or separation in the storage time.

EXAMPLE 2

Comparative Example

The B component of an impression material which does not contain any filler.

82 parts of a vinyl-terminated polydimethylsiloxane having a viscosity of 7.0 Pas at 20° C. are homogeneously mixed with 18 parts of a polymethylhydrogensiloxane having a viscosity of 0.2 Pas and a SiH contents of 1.8 mmol/g, and 0.02 parts of divinyltetramethyldisiloxane under vacuum in a vacuum mixer for 15 min.

One obtains a low-viscous paste having a viscosity of 4.6 Pas which does not have any thixothropy (thixotropic index: 1.0).

The rheological properties of the paste do not change, and naturally the paste does not feature any sedimentation or separation in the storage time.

EXAMPLE 3

Comparative Example

A mixture of the A component of example 1 and the B component of example 2.

50 parts of the A component of example 1 and 50 parts of the B component of example 2 are ejected from a double-chamber cartridge through a static mixer and homogeneously mixed. One obtains a low-viscous paste having a mixed viscosity of 5.0 Pas and no thixotropy (thixotropic index: 1.0). The paste has a processing time at 35° C. of 60 s and is completely cured at 35° C. after 240 s.

After the complete curing one obtains transparent, soft, slightly elastic and brittle, formed pieces. The recovery of shape after a deformation of the cured impression material according to ISO 4823 is 99.80%. The compression set according to ISO 4823 is 11.0%. The Shore A hardness is 18.

The tear resistance and the tear propagation resistance are not measurable since the test pieces cracked or fissured during the removal from the test piece form or the mounting in the testing apparatus.

The above-mentioned properties are insufficient for an impression material.

The material cracks or fissures during the removal from the mouth or the removal of the impression from the impression spoon.

Such a material is unsuited for the impression technique employing the novel impression spoon. The rheological and kinetic behavior of the impression material and the behavior thereof in the storage test with regard to sedimentation, separation and poststiffening is good, however, the mechanical strength of the obtained vulcanizate is completely insufficient.

EXAMPLE 4

Comparative Example

An A component of an impression material which contains only a reinforcing filler as a filler.

79 parts of a vinyl-terminated polydimethylsiloxane having a viscosity of 1.0 Pas at 20° C. are homogeneously mixed with 1 part of a platinum catalyst of the Karstedt type having a pure platinum content of 1% and 21 parts of a hydrophobized (surface-treated with trimethylsilyl groups), highly dispersed silicic acid having a BET surface of 140 $m^2/g$ under vacuum in a vacuum mixer for 60 min.

One obtains a low-viscous paste having a viscosity of 10.0 Pas and nearly no thixotropy (thixotropic index: 1.0). The paste exhibits a slight increase of the viscosity to 11.2 mPas and a constant thixotropy (thixotropic index: 1.0) in the storage time of one week. The paste does not sedimentate or separate in the storage time.

EXAMPLE 5

Comparative Example

A B component of an impression material which contains only a reinforcing filler as a filler.

58 parts of a vinyl-terminated polydimethylsiloxane having a viscosity of 0.2 Pas at 20° C. are homogeneously mixed with 27 parts of a branched polymethylhydrogensiloxane having a viscosity of 0.2 Pas and a SiH content of 4.3 mmol/g, 19 parts of a hydrophobized (surface-treated with trimethylsilyl groups), highly dispersed silicic add having a BET surface of 140 $m^2/g$ and 0.01 parts of a food dye under vacuum in a vacuum mixer for 60 min.

One obtains a low-viscous paste having a viscosity of 9.8 Pas and a low thixotropy (thixotropic index: 1.1). The paste exhibits a distinct increase of the viscosity to 15.0 mPas and a thixotropic index of 1.1 in the storage time of one week. The paste does not sedimentate or separate in the storage time.

EXAMPLE 6

Comparative Example

A mixture of the A component of example 4 and the B component of example 5.

50 parts of the A component of example 4 and 50 parts of the B component of example 5 are ejected from a double-chamber cartridge through a static mixer and homogeneously mixed. One obtains a low-viscous paste having a mixed viscosity of 9.0 Pas which does not have any thixotropy (thixotropic index; 1.0). The paste has a processing time at 35° C. of 30 s and is completely cured at 35° C. after 240 s.

After the complete curing, one obtains transparent, soft, elastic, formed pieces. The recovery of shape after a deformation of the cured impression material according to ISO 4823 is 99.60%. The compression set according to ISO 4823 is 5.45%. The Shore: A hardness is 37. The tear resistance and the tear propagation resistance are 103 $N/cm^2$ and 0.41 N/mm, resp.

The above-mentioned mechanical properties are insufficient for an impression material to be employed in the novel impression spoon. There is a risk that the material cracks or fissures during the removal from the mouth or the removal of the impression from the impression spoon.

The rheological features of the impression material after the storage test reveal a mixed viscosity of 8.3 Pas and a thixotropic index of 1.0 in the storage period (one week at 60° C.). The setting characteristics of the impression material are nearly unchanged in the storage time, This impression material is unsuited for the impression technique employing the novel impression spoon.

Although the rheological and kinetic behavior of the impression material and the behavior thereof in the storage test with regard to sedimentation, separation, and poststiffening are good, however, the mechanical strength of the obtained vulcanizates is completely insufficient.

EXAMPLE 7

Comparative Example

An A component of an impression material which contains only a non-reinforcing filler.

40 parts of a vinyl-terminated polydimethylsiloxane having a viscosity of 1000 mPas at 20° C. are homogeneously mixed with 1 part of a platinum catalyst of the Karstedt type having a pure platinum content of 1% and 59 parts of a silicon dioxide filler surface-treated with trimethylsilyl groups and having a BET surface of <1 $m^2/g$ and a mean particle size of 10 µm under vacuum in a vacuum mixer for 60 min.

One obtains a low-viscous paste having a viscosity of 8.7 Pas and a low thixotropy (thixotropic index: 1.1). In the storage time of one week, a distinct sedimentation of the filler and a separation of the silicone polymer occurs. Moreover, a slight increase of the viscosity to 11.8 Pas and of the thixotropy (thixotropic index: 1.1) occur in the storage test.

EXAMPLE 8

Comparative Example

A B component of an impression material which contains not only reinforcing filler as the filler.

29 parts of a vinyl-terminated polydimethylsiloxane having a viscosity of 1000 mPas at 20 °C. are homogeneously mixed with 6 parts of a polymethylhydrogensiloxane having a viscosity at 20° C. of 200 mPas and a SiH content of 1.8 mmol/g and 65 parts of a silicon dioxide filler (quartz) surface-treated with trimethylsilyl groups and having a BET surface of <1 $m^2/g$ and a mean particle size of 10 µm and 0.01 parts of a food dye under vacuum in a vacuum mixer for 60 min.

One obtains a low-viscous paste having a viscosity of 8.4 Pas and a low thixotropy (thixotropic index: 1.2). In the storage time of one week, a distinct sedimentation of the filler and separation of the silicone polymer occur. Moreover, nearly no increase of the viscosity of 8.6 Pas and of the thixotropy (thixotropic index: 1.2) occur in the storage test.

EXAMPLE 9

Comparative Example

A mixture of the A component of example 7 and the B component of example 8.

50 parts of the A component of example 7 and 50 parts of the B component of example 8 are ejected from a double-chamber cartridge through a static mixer and homogeneously mixed. One obtains a low-viscous paste having a mixed viscosity of 10.0 Pas and a low thixotropy (thixotropic index: 1.1). The paste has a processing time at 35° C. of 60 s and is completely cured at 35° C. after 230 s.

After the complete curing, one obtains relatively hard, formed pieces having a low elasticity. The recovery of shape after a deformation of the cured impression material according to ISO 4823 is 99.4%. The compression set according to ISO 4823 is 1,9%. The Shore A hardness is 73. The tear resistance and the tear propagation resistance are 308 $N/cm^2$ and 0.77 N/mm, resp.

For a tooth impression employing the novel impression spoon the tear resistance are at the upper limit, and the Shore A hardness is excessive so that the risk of a damage of the patient's attachment apparatus during the removal from the mouth exists. Due to a heavy sedimentation and separation of the fillers within the A and B single components (examples 16 and 17) in the storage time, the properties required for the mixed components are also no longer ensured. After storage, the mechanical and rheological properties and the setting behavior of the impression material may strongly be impaired by the sedimentation of the single components.

After the storage test of one week at 60° C., the rheological behavior of the impression material is characterized by a mixed viscosity of 10.2 Pas and a thixotropy (thixotropy index: 1.1). The setting characteristics of the impression material distinctly changes in the storage time.

This example illustrates that an impression material for the novel impression spoon is not suitable if only non-reinforcing fillers are used. In particular, the behavior concerning the sedimentation and the high Shore A hardness in the storage test make the use in the novel impression technique impossible.

EXAMPLE 10

Comparative Example

An A component of an impression material containing as fillers a combination of a high concentration of reinforcing and a low concentration of non-reinforcing fillers.

70 parts of a vinyl-terminated polydimethylsiloxane having a viscosity of 1000 mPas at 20° C. are homogeneously mixed with 1 part of a platinum catalyst of the Karstedt type having a pure platinum content of 1% and 24 parts of a hydrophobized (surface-treated with trimethylsilyl groups), highly dispersed silicic acid having a BET surface of 140 $m^2/g$ and 5 parts of a silicon dioxide filler (quartz) surface-treated with trimethylsilyl groups and having a BET surface of 1 $m^2/g$ and a mean particle size of 10 µm under vacuum in a vacuum mixer for 60 min. One obtains a low-viscous paste having a viscosity of 9.5 Pas and a low thixotropy (thixotropic index: 1.0). In the storage time of one week the paste has a low sedimentation of the filler, but no separation of the silicone polymer occurs. Moreover, in the storage test the viscosity distinctly increases to 13.4, whereas the thixotropy remains constant (thixotropic index: 1.0).

EXAMPLE 11

Comparative Example

A B component of an impression material containing as fillers a combination of a high concentration of reinforcing and a low concentration of non-reinforcing fillers.

47 parts of a vinyl-terminated polydimethylsiloxane having a viscosity of 1000 mPas at 20° C. are homogeneously mixed with 25 parts of a polymethylhydrogensiloxane having a viscosity at 20° C. of 200 mPas and a SiH content of 1.8 mmol/g and 23 parts of a hydrophobized (surface-treated with trimethylsilyl groups), highly dispersed silicic acid having a BET surface of 140 $m^2/g$, 5 parts of a silicon dioxide filler (quartz) surface-treated with trimethylsilyl groups and having a BET surface of <1 $m^2/g$ and a mean particle size of 10 µm, 0.02 parts of a food dye and 0.013 parts of divinyltetramethyldisiloxane under vacuum in a vacuum mixer for 60 min.

One obtains a low-viscous paste having a viscosity of 9.8 Pas and a thixotropic index of 1.0. In the storage time a slight sedimentation of the fillers, but no separation of the silicone polymers occurs. Moreover, a distinct increase of the viscosity to 17.9 Pas and of the thixotropy occurs in the storage test.

EXAMPLE 12

Comparative Example

A mixture of the A component of example 10 and the B component of example 11.

50 parts of the A component of example 10 and 50 parts of the B component of example 12 are ejected from a doublechamber cartridge through a static mixer and homogeneously mixed.

One obtains a low-viscous paste having a mixed viscosity of 9.2 Pas and a low thixotropy (thixotropic index: 1.1). The paste has a processing time at 35° C. of 60 s and is completely cured at 35° C. after 240 s.

After the complete curing, one obtains elastic, formed pieces having a Shore A hardness of 31. The recovery of shape after a deformation according to ISO 4823 is 99.4%. The compression set according to ISO 4823 is 6.4%. The tear resistance and the tear propagation resistance are 135 $N/cm^2$ and 2.59 N/mm, resp.

For a tooth impression employing the novel impression spoon the tear resistances are insufficient. There is the risk that the material cracks or fissures during the removal from the mouth or the removal of the impression from the impression spoon. The Shore A hardness is sufficient.

The rheological behavior of the impression material after the storage test of one week at 60° C. is characterized by an increase of the mixed viscosity to 10.7 Pas and a constant thixotropy (thixotropic index: 1.0).

The setting characteristics of the impression material do not change in the storage time.

This example illustrates that an impression material for the novel impression spoon is not suitable if a filler combination having a low concentration of non-reinforcing fillers and high concentrations of reinforcing fillers is used. The tear resistance of the cured impression material is too low and thus excludes a use in the novel impression spoon.

EXAMPLE 13

Comparative Example

An A component of an impression material containing as fillers a combination of a medium concentration of reinforcing and a medium concentration of non-reinforcing fillers.

51 parts of a vinyl-terminated polydimethylsiloxane having a viscosity of 1000 mPas at 20° C. are homogeneously mixed with 1 part of a platinum catalyst of the Karstedt type having a pure platinum content of 1% and 11 parts of a hydrophobized (surface-treated with trimethylsilyl groups), highly dispersed silicic acid having a BET surface of 140 $m^2/g$ and 37 parts of a silicon dioxide filler (quartz) surface-treated with trimethylsilyl groups and having a BET surface of <1 $m^2/g$ and a mean particle size of 10 µm under vacuum in a vacuum mixer for 60 min.

One obtains a low-viscous paste having a viscosity of 9.1 Pas and a thixotropic index of 1.1. In the storage time of one week the paste exhibits a medium sedimentation of the filler and a medium separation of the silicone polymer. Moreover, in the storage test the viscosity distinctly increases to 18.5 Pas, whereas the thixotropy remains constant.

EXAMPLE 14

Comparative Example

A B component of an impression material containing as a filler a combination of a medium concentration of reinforcing and a medium concentration of non-reinforcing fillers.

41 parts of a vinyl-terminated polydimethylsiloxane having a viscosity of 1000 mPas at 20° C. are homogeneously mixed with 13 parts of a polymethylhydrogensiloxane having a SiH content of 4.3 mmol/g and 10 parts of a hydrophobized (surface-treated with trimethylsilyl groups), highly dispersed silicic acid having a BET surface of 140 $m^2g$, 36 parts of a silicon dioxide filler (quartz) surface-treated with trimethylsilyl groups and having a BET surface of 1 $m^2/g$ and a mean particle size of 10 µm and 0.01 parts of a food dye under vacuum in a vacuum mixer for 60 min.

One obtains a low-viscous paste having a viscosity of 7.6 Pas and a thixotropic index of 1.2. The paste exhibits a slight sedimentation of the filler and a slight separation of the silicone polymer in the storage time of one week. Moreover, a distinct increase of the viscosity to 12.0 Pas occurs in the storage test, whereas the thixotropy remains constant.

EXAMPLE 15

Comparative Example

A mixture of the A component of example 13 and the B component of example 14.

50 parts of the A component of example 13 and 50 parts of the B component of example 14 are ejected from a double-chamber cartridge through a static mixer and homogeneously mixed.

One obtains a low-viscous paste having a mixed viscosity of 9.5 Pas and a thixotropic index of 1.0. The paste has a processing time at 35° C. of 40 s and is completely cured at 35° C. after 240 s.

After the complete curing, one obtains relatively hard, slightly elastic, formed pieces. The recovery of shape after a deformation according to ISO 4823 is 99.4%. The compression set according to ISO 4823 is 3.3%. The Shore A hardness is 54. The tear resistance and the tear propagation resistance are 203 $N/cm^2$ and 0,64 N/mm, resp. The tear resistance are well suited for a tooth impression employing the novel impression spoon, the Shore A hardness, however, is slightly excessive.

The rheological behavior of the impression material after the storage test of one week at 60° C. is characterized by an increase of the mixed viscosity to 13.9 Pas and of the thixotropy (thixotropic index: 1.4). The setting characteristics of the impression material do not change in the storage time. Due to the heavy sedimentation and separation of the fillers within the single components A and B (examples 13 and 14) in the storage time, also the required properties of the mixed components are no longer ensured.

After storage, the mechanical and rheological properties and the setting behavior of the impression material may severely be impaired due to the sedimentation of the single components.

This example illustrates that an impression material containing a filler combination with a medium concentration of reinforcing and non-reinforcing fillers is not suited for the novel impression spoon since the formulation has a distinct sedimentation of fillers and thus a storage stability is not attained. Due to the distinct thixotropy and the viscosity and thixotropy increases after storage, the flow behavior is not suited for a use in the novel impression spoon.

EXAMPLE 16

Comparative Example

An A component of an impression material containing as fillers a combination of a low concentration of reinforcing fillers and a high concentration of non-reinforcing fillers.

47 parts of a vinyl-terminated polydimethylsiloxane having a viscosity of 1000 mPas at 20° C. are homogeneously mixed with 1 part of a platinum catalyst of the Karstedt type having a pure platinum content of 1% and 4 parts of a hydrophobized, highly dispersed silicic acid having a BET surface of 140 m²/g and 48 parts of a silicon dioxide filler (quartz) surface-treated with trimethylsilyl groups and having a BET surface of <1 m²/g and a mean particle size of 10 μm under vacuum in a vacuum mixer for 60 min.

One obtains a low-viscous paste having a viscosity of 9.0 Pas and a thixotropic index of 1.0. In the storage time of one week the paste exhibits a heavy sedimentation of the fillers and a heavy separation of the silicone polymer. Moreover, in the storage test an increase of the viscosity to 11.0 Pas and of the thixotropy (thixotropic index: 1.1) occurs.

EXAMPLE 17

Comparative Example

A B component of an impression material containing as fillers a combination of a low concentration of reinforcing fillers and a high concentration of non-reinforcing fillers.

26 parts of a vinyl-terminated polydimethylsiloxane having a viscosity of 1000 mPas at 20° C. are homogeneously mixed with 16 parts of a polymethylhydrogensiloxane having a viscosity at 20° C. of 200 mPas and a SiH content of 1.8 mmol/g and 4 parts of a hydrophobized (surface-treated with trimethylsilyl groups), highly dispersed silicic acid having a BET surface of 140 m²/g, 54 parts of a silicon dioxide filler (quartz) surface-treated with trimethylsilyl groups and having a BET surface of 1 m²/g and a mean particle size of 10 μm, 0.02 parts of a food dye and 0.02 parts of divinyltetramethyldisiloxane under vacuum in a vacuum mixer for 60 min.

One obtains a low-viscous paste having a viscosity of 9.9 Pas and a thixotropic index of 1.3. The paste exhibits a heavy sedimentation of the filler and a heavy separation of the silicone polymers in the storage time. Moreover, a distinct increase of the viscosity to 15 Pas and of the thixotropy (thixotropic index: 1.5) occurs in the storage test.

EXAMPLE 18

Comparative Example

A mixture of the A component of example 16 and the B component of example 17.

50 parts of the A component of example 16 and 50 parts of the B component of example 17 are ejected from a double-chamber cartridge through a static mixer and homogeneously mixed.

One obtains a low-viscous paste having a mixed viscosity of 8.5 Pas and a thixotropic index of 1.1 The paste has a processing time at 35° C. of 60 s and is completely cured at 35° C. after 240 s. After the complete curing one obtains elastic, formed pieces having a Shore A hardness of 57.

The recovery of shape after a deformation according to ISO 4823 is 99.70%. The compression set according to ISO 4823 is 2.7%. The tear resistance and the tear propagation resistance are 272 N/cm² and 0,73 N/mm, resp. The tear resistance and the Shore A hardness are well suited for a tooth impression employing the novel impression spoon.

The rheological behavior of the impression material after the storage test of one week at 60° C. is characterized by an increase of the mixed viscosity to 12.4 Pas and a constant thixotropy (thixotropic index: 1.1). In the storage time, the setting time of the impression material decreases to 185 s.

Due to the strong sedimentation and separation of the fillers within the single components A and B (examples 16 and 17) in the storage time, also the required properties of the mixed components are no longer ensured.

After storage, the mechanical and rheological properties and the setting behavior of the impression material will severely be impaired due to the sedimentation of the single components.

This example illustrates that an impression material containing a filler combination with low concentrations of reinforcing fillers and high concentrations of non-reinforcing fillers is not suited for the novel impression spoon.

EXAMPLE 19

Comparative Example

An A component of an impression material containing as filers a combination of a low concentration of reinforcing fillers (BET surface; 200 m²/g) and a high concentration of non-reinforcing fillers.

54 parts of a vinyl-terminated polydimethylsiloxane having a viscosity of 1000 mPas at 20° C. are homogeneously mixed with 1 part of a platinum catalyst of the Karstedt type having a pure platinum content of 1% and 4 parts of a hydrophobized (surface-treated with trimethylsilyl groups), highly dispersed silicic acid having a BET surface of 200 m²/g and 41 parts of a silicon dioxide filler (quartz) surface-treated with trimethylsilyl groups and having a BET surface of <1 m²/g and a mean particle size of 10 μm under vacuum in a vacuum mixer for 60 min.

One obtains a low-viscous paste having a viscosity of 8.5 Pas and a thixotropic index of 1.1. In the storage of one week at 60° C. the paste exhibits a heavy sedimentation of the fillers and a heavy separation of the silicone polymer, Moreover, in the storage test a distinct increase of the viscosity to 8.8 Pas occurs, whereas the thixotropy remains constant.

EXAMPLE 20

Comparative Example

A B component of an impression material containing as fillers a combination of a low concentration of reinforcing fillers (BET surface: 200 m²/g) and a high concentration of non-reinforcing fillers.

34 parts of a vinyl-terminated polydimethylsiloxane having a viscosity of 1000 mPas at 20° C. are homogeneously mixed with 20 parts of a polymethylhydrogensiloxane having a viscosity at 20° C. of 200 mPas and a SiH content of 1.8 mmol/g and 4 parts of a hydrophobized (surface-treated with trimethylsilyl groups), highly dispersed silicic acid having a BET surface of 200 m²/g, 42 parts of a silicon dioxide filler (quartz) surface-treated with trimethylsilyl groups and having a BET surface of <1 m²/g and a mean particle size of 10 μm, 0.02 parts of a food dye and 0.02 parts of divinyltetramethyldisiloxane under vacuum in a vacuum mixer for 60 min.

One obtains a low-viscous paste having a viscosity of 9.4 Pas and a thixotropic index of 1.2. The paste exhibits a heavy sedimentation of the fillers and a heavy separation of the silicone polymers in the storage time. Moreover, a distinct increase of the viscosity to 13.4 Pas and of the thixotropy (thixotropic index: 1.7) occurs in the storage test.

EXAMPLE 21

Comparative Example

A mixture of the A component of example 19 and the B component of example 20.

50 parts of the A component of example 19 and 50 parts of the B component of example 20 are ejected from a double-chamber cartridge through a static mixer and homogeneously mixed.

One obtains a low-viscous paste having a mixed viscosity of 6.4 Pas and a thixotropic index of 1.1. The paste has a processing time at 35° C. of 60 s and is completely cured at 35° C. after 230 s. After the complete curing one obtains elastic, formed pieces having a Shore A hardness of 51.

The recovery of shape after a deformation according to ISO 4823 is 99.60%. The compression set according to ISO 4823 is 3.4%. The tear resistance and the tear propagation resistance are 170 N/cm$^2$ and 0,59 N/mm, resp. Directly after the preparation of the tooth impression material, the tear resistance and the Shore A hardness are well suited for an impression employing the novel impression spoon material.

The rheological behavior of the impression material after the storage test of one week at 60° C. is characterized by an increase of the mixed viscosity to 7.6 Pas and of the thixotropy. In the storage time, the setting time of the impression material decreases to 175 s.

Due to the strong sedimentation and separation of the fillers within the single components A and B (examples 19 and 20) in the storage time, also the required properties of the mixed components are no longer ensured.

After storage, the mechanical and rheological properties and the setting behavior of the impression material will severely be impaired due to the sedimentation of the single components.

This example illustrates that an impression material containing a filler combination with low concentrations of reinforcing fillers (BET surface: 200 m$^2$/g) and high concentrations of non-reinforcing fillers is not suited for the novel impression spoon.

EXAMPLE 22

Comparative Example

An A component of an impression material containing as a filler only a reinforcing filler (BET surface: 200 m$^2$/g).

91 parts of a vinyl-terminated polydimethylsiloxane having a viscosity of 1.0 Pas at 20° C. are homogeneously mixed with 1 part of a platinum catalyst of the Karstedt type having a pure platinum content of 1% and 8 parts of a hydrophobized (surface-treated with trimethylsilyl groups), highly dispersed silicic acid having a BET surface of 200 m$^2$/g under vacuum in a vacuum mixer for 60 min.

One obtains a low-viscous paste having a viscosity of 9.2 Pas and a thixotropic index of 1.0. In the storage time of one week, the paste exhibits nearly no change of the viscosity and the thixotropy.

Naturally, the paste has no sedimentation or separation in the storage time.

EXAMPLE 23

Comparative Example

A B component of an impression material containing only a reinforcing filler (BET surface; 200 m$^2$/g) as a filler.

58 parts of a vinyl-terminated polydimethylsiloxane having a viscosity of 1.0 Pas at 20° C. are homogeneously mixed with 32 parts of a polymethylhydrogensiloxane having a viscosity at 20° C. of 0.2 Pas and a SiH content of 1.8 mmol/g and 10 parts of a hydrophobized (surface-treated with trimethylsilyl groups), highly dispersed silicic acid having a BET surface of 200 m$^2$/g and 0.01 parts of a food dye under vacuum in a vacuum mixer for 60 min.

One obtains a low-viscous paste having a viscosity of 9.1 Pas and a thixotropic index of 1.0. The paste exhibits nearly no viscosity and thixotropy changes after the storage time of one week.

In the storage test no sedimentation or separation of the paste occurs.

EXAMPLE 24

Comparative Example

A mixture of the A component of example 22 and the B component of example 23.

50 parts of the A component of example 22 and 50 parts of the B component of example 23 are ejected from a double chamber cartridge through a static mixer and homogeneously mixed.

One obtains a low-viscous paste having a mixed viscosity of 7.1 Pas and a thixotropic index of 1.1. The paste has a processing time at 35° C. of 60 s and is completely cured at 35° C. after 240 s.

After the complete curing, one obtains transparent, soft, elastic, formed pieces. The recovery of shape after a deformation according to ISO 4823 is 99.70%. The compression set according to ISO 4823 is 6.4%. The Shore A hardness is 31. The tear resistance and the tear propagation resistance are 40 N/cm$^2$ and 0,32 N/mm, resp.

For a tooth impression employing the novel impression spoon the mechanical properties are insufficient. There is the risk that the material cracks or fissures during the removal from the mouth or the removal of the impression from the impression spoon.

The rheological behavior of the impression material after the storage test is characterized by a mixed viscosity to 7.4 Pas and a thixotropic index of 1.0 after storage (1 week at 60° C.). In the storage time, the setting characteristics of the impression material changes to an setting time of 280 s.

EXAMPLE 25

According to the Invention

An A component of an impression material of the invention for the novel impression spoon having a mixed viscosity of about 7.5 Pas.

72 parts of a vinyl-terminated polydimethylsiloxane having a viscosity of 1000 mPas at 20° C. are homogeneously mixed with 1 part of a platinum catalyst of the Karstedt type having a pure platinum content of 1% and 25 parts of a hydrophilic, wet-precipitated silicic acid having calcium oxide content of 6% and a BET surface of 35 m$^2$/g, which was brought to a residual water content of 0.3% by a 48 h drying at 130° C., and 2 parts of a hydrophobized (surface-treated with trimethylsilyl groups), highly dispersed silicic acid having a BET surface of 140 m$^2$/g under vacuum in a vacuum mixer for 60 min.

One obtains a low-viscous paste having a viscosity of 6.7 Pas and a thixotropic index of 1.1. In the storage time of three weeks at 60° C., the paste exhibits no sedimentation of the fillers and no separation of the silicone polymers.

In the storage test, the viscosity increases to 8.1 Pas and the thixotropy increases (thixotropic index: 1.4).

EXAMPLE 26

According to the Invention

A B component of an impression material of the invention for the novel impression spoon having a mixed viscosity of about 7.5 Pas.

47 parts of a vinyl-terminated polydimethylsiloxane having a viscosity of 1000 mPas at 20° C. are homogeneously mixed with 26 parts of a polymethylhydrogensiloxane hydrogensiloxane having a viscosity at 20° C. of 200 mPas and a SiH content of 1.80 mmol/g, 25 parts of a hydrophilic, wet-precipitated silicic acid having a calcium oxide content of 6% and a BET surface of 35 m²/g, which was brought to a residual water content of 0.3% by a 48 h drying at 130° C., and 2 parts of a hydrophobized (surface-treated with trimethylsilyl groups), highly dispersed silicic acid having a BET surface of 140 m²/g under vacuum in a vacuum mixer for 60 min.

One obtains a low-viscous paste having a viscosity of 7.3 Pas and a thixotropic index of 1.0. In the storage time of three weeks at 60° C., the paste exhibits no sedimentation of the fillers and no separation of the silicone polymers.

In the storage test, the viscosity increases to 7.9 Pas: and the thixotropy slightly increases (thixotropic index: 1.1).

EXAMPLE 27

According to the Invention

A mixture of the A component of example 25 and the B component of example 26.

50 parts of the A component of example 25 and 50 parts of the B component of example 26 are ejected from a double-chamber cartridge through a static mixer and homogeneously mixed.

One obtains a low-viscous paste having a mixed viscosity of 7.3 Pas and a thixotropic index of 1.1. The paste has a processing time at 35° C. of 60 s and is completely cured at 35° C. after 215 s.

After the complete curing, one obtains elastic, formed pieces having a Shore A hardness of 41. The recovery of shape after a deformation according to ISO 4823 is 99.90%. The compression set according to ISO 4823 is 6.40%. The tear resistance and the tear propagation resistance are 225 N/cm² and 0,59 N/mm, resp.

The mechanical properties are very well suited for a tooth impression employing the novel impression spoon. The removal from the mouth can gently be performed without any risk for the Patient's attachment apparatus. Due to the high tear resistance thereof, the cured material does not exhibit any unwanted fissuring during the removal from the mouth or the removal of the impression from the impression spoon, The rheological behavior of the inventive impression material after the storage test is characterized by a constant thixotropy (thixotropic index: 1.1). Also the setting behavior of the impression material does not change in the storage time.

Thus, it is ensured that the very good flow behavior and with that the precision of the impression results will be maintained also in the storage time of the impression material of the invention.

When using the impression material of the invention in the novel impression spoon in the patient's mouth, one obtains excellent, highly precise impression results.

This example illustrates that an impression material for the novel impression spoon is very well suited with regard to the rheological properties, the mechanical properties, the kinetic behavior and the behavior in the storage test when employing the filler to be used according to the invention having a BET surface of from 20 to 50 m²/g.

EXAMPLE 28

According to the Invention

An A component of an impression material for the novel impression spoon, wherein the filler of the invention was employed undried.

72 parts of a vinyl-terminated polydimethylsiloxane having a viscosity of 1000 mPas at 20° C. are homogeneously mixed with 1 part of a platinum catalyst of the Karstedt type having a pure platinum content of 1% and 25 parts of a hydrophilic, wet-precipitated silicic add having calcium oxide content of 6% and a BET surface of 35 m²/g, which is employed undried and has a water content of 6,0%, 2 parts of a hydrophobized (surface-treated with trimethylsilyl groups), highly dispersed silicic acid having a BET surface of 140 m²/g under vacuum in a vacuum mixer for 60 min.

One obtains a low-viscous paste having a viscosity of 6.7 Pas and a thixotropic index of 1.1. In the storage time of one week at 60° C., the paste exhibits no sedimentation of the fillers and no separation of the silicone polymers.

In the storage test, the viscosity increases to 8.1 Pas and the thixotropy increases (thixotropic index: 1.4).

Already after a storage time at 60° C. of one week, the paste has a brown discoloration due to a decomposition of the platinum catalyst. This is due to the presence of water in the undried filler.

EXAMPLE 29

According to the Invention

A B component of an impression material of the invention for the novel impression spoon.

47 parts of a vinyl-terminated polydimethylsiloxane having a viscosity of 1000 mPas at 20° C. are homogeneously mixed with 26 parts of a polymethylhydrogensiloxane hydrogensiloxane having a viscosity at 20° C. of 200 mPas and a SiH content of 1.80 mmol/g, 25 parts of a hydrophilic, wet-precipitated silicic acid having a calcium oxide content of 6%, a BET surface of 35 m²/g, and a water content of 6% which was brought to a residual water content of 0.3% by a 48 h drying at 130° C., and 2 parts of a hydrophobized (surface-treated with trimethylsilyl groups), highly dispersed silicic acid having a BET surface of 140 m²/g under vacuum in a vacuum mixer for 60 min.

One obtains a low-viscous paste having a viscosity of 7.3 Pas and a thixotropic index of 1.0. In the storage time of three weeks at 60° C., the paste exhibits no sedimentation of the fillers and no separation of the silicone polymers. In the storage test, the viscosity increases to 7.9 Pas and the thixotropy slightly increases (thixotropic index: 1.1).

Already after a storage of one week at 60° C., the aluminium tubes used as storage packages are distinctly swollen. This is due to the hydrogen developed during the reaction of the SiH crosslinking agent with the water contained in the filler.

EXAMPLE 30

According to the Invention

A mixture of the A component of example 28 and the B component of example 29.

50 parts of the A component of example 28 and 50 parts of the B component of example 29 are ejected from a double-chamber cartridge through a static mixer and homogeneously mixed.

One obtains a low-viscous paste having a mixed viscosity of 7.3 Pas and a thixotropic index of 1.1.

Immediately after the preparation, the paste has the same positive properties as the impression material of example 27.

However, after a one week storage at 60° C. the impression material suffers from a severe increase of the setting time as compared with the initial value of 215 s (end of setting: 600 s) due to the instabilities of the single components caused by the high water content of the filler described in examples 28 and 29.

Therefore, a use of the filler to be used according to the invention in an undried form for an impression material to be employed in the new impression spoon is not optimal.

EXAMPLE 31

According to the Invention

An A component of an inventive impression material for the novel impression spoon having a mixed viscosity of about 40 Pas.

72 parts of a vinyl-terminated polydimethylsiloxane having a viscosity of 7,0 Pas at 20° C. are homogeneously mixed with 1 part of a platinum catalyst of the Karstedt type having a pure platinum content of 1% and 25 parts of a hydrophilic, wet-precipitated silicic acid having calcium oxide content of 6% and a BET surface of 35 $m^2/g$, which was brought to a residual water content of 0.3% by a 48 h drying at 130° C., and 2 parts of a hydrophobized (surface-treated with trimethylsilyl groups), highly dispersed silicic acid having a BET surface of 140 $m^2/g$ under vacuum in a vacuum mixer for 60 min.

One obtains a low-viscous paste having a viscosity of 36,8 Pas and a thixotropic index of 1.2. In the storage time of three weeks at 60° C., the paste exhibits no sedimentation of the fillers and no separation of the silicone polymers.

In the storage test, the viscosity increases to 38,2 Pas and the thixotropy remains nearly constant (thixotropic index: 1.2).

EXAMPLE 32

According to the Invention

A B component of an impression material of the invention for the novel impression spoon having a mixed viscosity of about 40 Pas.

60 parts of a vinyl-terminated polydimethylsiloxane having a viscosity of 7.0 Pas at 20° C. are homogeneously mixed with 13 parts of a polymethylhydrogensiloxane having a SiH content of 1.8 mmol/g, 25 parts of a hydrophilic, wet-precipitated silicic acid having a calcium oxide content of 6% and a BET surface of 35 $m^2/g$, which was brought to a residual water content of 0.3% by a 48 h drying at 130° C., and 2 parts of a hydrophobized (surface-treated with trimethylsilyl groups), highly dispersed silicic acid having a BET surface of 140 $m^2/g$ under vacuum in a vacuum mixer for 60 min.

One obtains a low-viscous paste having a viscosity of 25.5 Pas and a thixotropic index of 1.1. In the storage time of three weeks at 60° C., the paste exhibits no sedimentation of the fillers and no separation of the silicone polymers.

In the storage test, the viscosity increases to 28.4 Pas and the thixotropy slightly increases (thixotropic index: 1.2).

EXAMPLE 33

According to the Invention

A mixture of the A component of example 31 and the B component of example 32 having a mixed viscosity of about 40 Pas.

50 parts of the A component of example 31 and 50 parts of the B component of example 32 are ejected from a double-chamber cartridge through a static mixer and homogeneously mixed.

One obtains a low-viscous paste having a mixed viscosity of 39.8 Pas and a thixotropic index of 1.1.

The paste has a processing time at 35° C. of 60 s and is completely cured at 35° C. after 180 s.

After the complete curing, one obtains elastic, formed pieces having a Shore A hardness of 35. The recovery of shape after a deformation according to ISO 4823 is 4,60%. The tear resistance and the tear propagation resistance are 174 $N/cm^2$ and 2.09 N/mm, resp, The mechanical properties are very well suited for an impression employing the novel impression spoon. The removal from the mouth can gently be performed without any risk for the Patient's attachment apparatus. Due to the high tear resistance thereof, the cured material does not exhibit any unwanted fissuring during the removal from the mouth or the removal of the impression from the impression spoon. The rheological behavior of the inventive impression material after the storage test is characterized by a nearly unchanged mixed viscosity of 39.9 Pas and a constant thixotropy (thixotropic index: 1.1). Also the setting behavior of the impression material does not change in the storage time.

Thus, it is ensured that the very good flow behavior and with that the precision of the impression will be maintained also in the storage time of the impression material of the invention.

When using the impression material of the invention in the novel impression spoon in the patient's mouth, one obtains excellent, highly precise impression results.

This example illustrates that an impression material for the novel impression spoon having a mixed viscosity of 40 Pas is very well suited with regard to the rheological properties, the kinetic behavior and the behavior in the storage test when employing the filler to be used according to the invention having a BET surface of from 20 to 50 $m^2/g$. In comparison with example 27, one obtains not very good, but only good impression results due to the higher mixed viscosity of 40 Pas. This lower quality becomes apparent in difficult preparation situations existing behind voluminous teeth at the side averted from the flow direction. Here, the flowing around these difficultly accessible areas may be incomplete. This manifests itself in defects in the finished impression. This effect does not occur in example 27 according to the invention having the especially preferred viscosity range of from 1 to 10 Pas,

EXAMPLE 34

Comparative Example

An A component of a commercial, low-viscous tooth impression material used for conventional impression techniques (material for correction impressions).

The A component exists as a low-viscous paste having a viscosity of 10.9 Pas and a high thixotropy (thixotropic index: 9.0).

During a one week storage at 60° C., the viscosity of the paste distinctly increases to 23.0 Pas, whereas the thixotropy is still high (thixotropic index: 5.7).

In the storage time, the paste exhibits no sedimentation of the fillers and no separation of the silicone polymers.

EXAMPLE 35

Comparative Example

The B component of a commercial, low-viscous tooth impression material (material for correction impressions) used in conventional impression techniques.

The B component exists as a low-viscous paste having a viscosity of 16 Pas and a high thixotropy (thixotropic index: 49.0).

In a one week storage at 60° C., the paste exhibits an increase of the viscosity to 20.0 Pas and of the thixotropy (thixotropic index: 63.8).

In the storage time, the paste exhibits no sedimentation of the fillers and no separation of the silicone polymers.

EXAMPLE 36

Comparative Example

A mixture of the A component of example 34 and the B component of example 35 (commercial impression materials for conventional impression techniques).

50 parts of the A component of example 34 and 50 parts of the B component of example 35 are ejected from a double-chamber cartridge through a static mixer and homogeneously mixed.

One obtains a low-viscous paste having a mixed viscosity of 38.9 Pas and a thixotropic index of 1.7.

The paste has a processing time at 35° C. of 60 s and is completely cured at 35° C. after 150 s. After the complete curing, one obtains elastic, formed pieces having a Shore A hardness of 46. The recovery of shape after a deformation according to ISO 4823 is 99.80%. The compression set according to ISO 4823 is 4,60%. The tear resistance and the tear propagation resistance are 200 N/cm² and 2.09 N/mm, resp. The mechanical properties would be well suited for a tooth impression employing the novel impression spoon. However, when used in the novel impression spoon in the patient's mouth, the strongly thixotropic flow properties of the commercial impression material result in flow trails when the material flows around the teeth in the areas averted from the flow direction, and these flow trails severely falsify the impression result. A use in the novel impression spoon is not advantegeous.

EXAMPLE 37

According to the Invention

The B component of an impression material of the invention for the novel impression spoon having a mixed viscosity of about 7.5 Pas.

46 parts of a vinyl-terminated polydimethylsiloxane having a viscosity of 7000 mPas at 20° C. are homogeneously mixed with 20 parts of a polymethylhydrogensiloxane having a viscosity at 20° C. of 200. mPas and a SiH content of 1.8 mmol/g, 7 parts of a polysiloxane-polyether copolymer having a viscosity of 200 mPas and vinyl content of 0.15 mmol/g, 25 parts of a hydrophilic, wet-precipitated silicic acid having a calcium oxide content of 6% and a BET surface of 35 m²/g, which was brought to a residual water content of 0.3% by a 48 h drying at 130° C., and 2 parts of a hydrophobized (surface-treated with trimethylsilyl groups), highly dispersed silicic acid having a BET surface of 140 m²/g under vacuum in a vacuum mixer for 60 min.

One obtains a low-viscous paste having a viscosity of 7.3 Pas and a thixotropic index of 1.0. In the storage time of three weeks at 60° C., the paste exhibits no sedimentation of the fillers and no separation of the silicone polymers. In the storage test, the viscosity increases to 7.9 Pas and the thixotropy slightly increases (thixotropic index: 1.1).

EXAMPLE 38

According to the Invention

A mixture of the A component of example 25 and the B component of example 37.

50 parts of the A component of example 25 and 50 parts of the B component of example 37 are ejected from a double-chamber cartridge through a static mixer and homogeneously mixed.

One obtains a low-viscous paste having a mixed viscosity of 7.3 Pas and a thixotropic index of 1.1. The paste has a processing time at 35° C. of 60 s and is completely cured at 35° C. after 215 s.

After the complete curing, one obtains elastic, formed pieces having a Shore A hardness of 41. The recovery of shape after a deformation according to ISO 4823 is 99.90%. The compression set according to ISO 4823 is 6.40%. The tear resistance and the tear propagation resistance are 225 N/cm² and 0.59 N/mm, resp.

The mechanical properties are well suited for a tooth impression employing the novel impression spoon. The removal from the mouth can gently be performed without any risk for the Patient's attachment apparatus. Due to the high tear resistance thereof, the cured material does not exhibit any unwanted fissuring during the removal from the mouth or the removal of the impression from the impression spoon. The rheological behavior of the inventive impression material after the storage test is characterized by a unchanged thixotropy (thixotropic index: 1.1). Also the setting behavior of the impression material does not change in the storage time.

Thus, it is ensured that the very good flow behavior and with that the precision of the impression will be maintained also in the storage time of the impression material of the invention.

When using the impression material of the invention in the novel impression spoon in the patient's mouth, one obtains excellent, highly precise impression results.

This example illustrates that an impression material for the novel impression spoon is very well suited with regard to the rheological properties, the mechanical properties, the kinetic behavior and the behavior in the storage test when employing the filler to be used according to the invention having a BET surface of from 20 to 50 m²/g.

In addition, this example illustrates that the inventive filler exerts its outstanding properties with regard to the sedimentation and separation behaviors and the thixotropy of the mixture with the use of a silicone polyether. Moreover, the filler of the invention suppresses the natural demixing tendency of a silicone polyether in a silicone copolymer matrix. Due to the hydrophilic properties of the silicone polyether, the use thereof in turn results in excellent impression results during the curing within the patient's mouth. The silicone polyether is incorporated in the network during the curing of the two-component material of the invention and therefore not washed out during the disinfection of the finished impression. This, in turn, results in a good flowing of the plaster around the impression during the subsequent casting with aqueous thin plaster and with that in an excellent quality of the model.

TABLE 1 technical data of the examples (single components)

Examples 1 to 23, 28, 29, 34, and 35 are comparative examples
Examples 25, 26, 31, and 32 are examples according to the invention

| | | | | Storage tests RT/60° C. | | | |
|---|---|---|---|---|---|---|---|
| | Description | Viscosity[1] [Pas] | Thixotropic index[2] | Sedimentation only at RT | Separation only at RT | Viscosity 1 week at 60° C. [Pas] | Thixotropic index 1 week at 60° C. |
| Ex. 1 | Without fillers, component A | 6.4 | 1.0 | None | None | 6.4 | 1.0 |
| Ex. 2 | Without fillers, component B | 4.6 | 1.0 | None | None | 4.6 | 1.0 |
| Ex. 4 | Only reinforcing fillers, BET: 140 m²/g, A component | 10.0 | 1.0 | None | None | 11.2 | 1.0 |

TABLE 1-continued technical data of the examples (single components)

Examples 1 to 23, 28, 29, 34, and 35 are comparative examples
Examples 25, 26, 31, and 32 are examples according to the invention

|  | Description | Viscosity[1] [Pas] | Thixotropic index[2] | Sedimentation only at RT | Separation only at RT | Viscosity 1 week at 60° C. [Pas] | Thixotropic index 1 week at 60° C. |
|---|---|---|---|---|---|---|---|
| Ex. 5 | Only reinforcing fillers, BET: 140 m²/g, B component | 9.8 | 1.1 | None | None | 15.0 | 1.1 |
| Ex. 7 | Only non-reinf. fillers, BET: 140 m²/g, A component | 8.7 | 1.1 | Severe | Severe | 11.8 | 1.1 |
| Ex. 8 | Only non-reinf. fillers, BET: 140 m²/g, B component | 8.4 | 1.2 | Severe | severe | 8.6 | 1.2 |
| Ex. 10 | High conc. of reinf. fillers, low conc. of non-reinf. fillers, A component | 9.5 | 1.0 | None | None | 13.4 | 1.0 |
| Ex. 11 | High conc. of reinf. fillers, low conc. of non-reinf. fillers, B component | 9.5 | 1.0 | None | None | 17.9 | 1.0 |
| Ex. 13 | Medium conc. of reinf. fillers, medium conc. of non-reinf. fillers, A component | 9.1 | 1.1 | Medium | Medium | 18.5 | 1.1 |
| Ex. 14 | Medium conc. of reinf. fillers, medium conc. of non-reinf. fillers, B component | 7.6 | 1.2 | Medium | Medium | 12.0 | 1.2 |
| Ex. 16 | Low conc. of reinf. fillers, high conc. of non-reinf. fillers, A component | 9.0 | 1.0 | Severe | Severe | 11.0 | 1.1 |
| Ex. 17 | Low conc. of reinf. fillers, high conc. of non-reinf. fillers, B component | 9.9 | 1.3 | Severe | Severe | 15.7 | 1.5 |
| Ex. 18 | Low conc. of reinf. fillers, high conc. of non-reinf. fillers, BET: 200 m²/g, A component | 8.5 | 1.1 | Severe | Severe | 8.6 | 1.1 |
| Ex. 20 | Low conc. of reinf. fillers, high conc. of non-reinf. fillers, BET: 200 m²/g, B component | 9.4 | 1.2 | Severe | Severe | 13.4 | 1.7 |
| Ex. 22 | Only reinforcing fillers, BET: 200 m²/g, A component | 9.2 | 1.0 | None | None | 9.2 | 1.0 |
| Ex. 23 | Only reinforcing fillers, BET: 200 m²/g, B component | 9.1 | 1.0 | None | None | 9.1 | 1.1 |
| Ex. 25 | Inventive impression material, A component, 7.5 Pas | 6.7 | 1.1 | None | None | 8.1 | 1.4 |
| Ex. 26 | Inventive impression material, B component, 7.5 Pas | 7.3 | 1.0 | None | None | 7.9 | 1.1 |
| Ex. 28 | As example 25, but undried filler | 6.7 | 1.1 | None | None | 8.1 | 1.4 |
| Ex. 29 | As example 26, but undried filler | 7.3 | 1.0 | None | None | 7.9 | 1.1 |
| Ex. 31 | Inventive impression material, A component, 40 Pas | 36.8 | 1.2 | None | None | 38.2 | 1.1 |
| Ex. 32 | Inventive impression material, B component, 40 Pas | 25.5 | 1.1 | None | None | 28.4 | 1.2 |
| Ex. 34 | Commerical low-viscous correction impression material, A | 10.9 | 9.0 | Moderate | Moderate | 23.0 | 5.7 |
| Ex. 35 | Commercial low-viscous correction impression material, B | 16.0 | 49.0 | Moderate | Moderate | 20.0 | 64.0 |

[1] The viscosity is measured using a RS 150 viscosimeter of the Haake company at 23° C. Oscillation frequency: 1 Hz; cone plate system; 35 mm; 4° cone; shear stress: 50 Pa; for evaluation, the viscosity value is read off after a measuring time of 80 s.

TABLE 2 technical data of the examples (single components)[1]

Examples 3 to 24, 30, and 36 are comparative examples
Examples 27 and 33 are examples according to the invention

|  | Example 3 | Example 6 | Example 9 | Example 12 | Example 15 | Example 18 |
|---|---|---|---|---|---|---|
| Description | Without fillers | Only reinforcing fillers (BET: 140 m²/g) | Only non-reinforcing fillers | High concentration of reinforcing, low conc. of non-reinforcing fillers | Medium concentration of reinforcing and non-reinforcing fillers | Low concentration of reinforcing (BET: 140 m²/g), high conc. of non-reinforcing fillers |
| Mixed viscosity[9] | 5.0 Pas | 9.0 Pas | 10.0 Pas | 9.2 Pas | 9.5 Pas | 8.5 Pas |
| Thixotropic index of the mixture[8] | 1.0 | 1.0 | 1.1 | 1.1 | 1.0 | 1.1 |
| Processing time[10] | 60 s | 30 s | 60 s | 60 s | 40 s | 60 s |
| End of setting[11] | 240 s | 270 s | 230 s | 240 s | 270 s | 230 s |
| Recovery of shape (ISO 4823) | 99.80% | 99.60% | 99.40% | 99.40% | 99.40% | 99.70% |
| Plasticity and pressure (ISO 4823) | 11.00% | 5.50% | 1.90% | 6.40% | 3.30% | 2.70% |
| Shore A hardness[12] | 18 | 34 | 73 | 31 | 54 | 57 |
| Tear resistance[13] | [7] | 103 N/cm² | 308 N/cm² | 135 N/cm² | 203 N/cm² | 272 N/cm² |
| Tear propagation strength[14] | 0.1 N/mm | 0.41 N/mm | 0.77 N/mm | 2.59 N/mm | 0.64 N/mm | 0.73 N/mm |

TABLE 2-continued technical data of the examples (single components)[1]

Examples 3 to 24, 30, and 36 are comparative examples
Examples 27 and 33 are examples according to the invention

| Impression result employing the novel impression spoon[15] | Insufficient too brittle[3] | Poor too brittle[3] | Insufficient too hard sedimentates[4] | Poor too brittle[3] | Poor sedimentates[4] | Poor sedimentates[4] |
|---|---|---|---|---|---|---|
| End of setting, 1 week, 60° C. | 220 s | 260 s | 270 s | 240 s | 270 s | 185 s |
| Mixed viscosity, 1 week, 60° C. | 4.6 Pas | 6.3 Pas | 10.2 Pas | 10.7 Pas | 13.9 Pas | 12.4 Pas |
| Thixotropic index, 3 weeks, 60° C. | 1.0 | 1.0 | 1.1 | 1.0 | 1.4 | 1.1 |

|  | Example 21 | Example 24 | Example 27 | Example 30 | Example 33 | Example 36 |
|---|---|---|---|---|---|---|
| Description | Low concentration or reinforcing (BET: 200 m²/g), high conc. of non-reinforcing fillers | Only reinforcing fillers (BET: 200 m²/g) | According to the invention, 7.5 Pas, BET: 35 m²/g | Comprising the inventive filler, but undried | According to the invention, 40 Pas, BDT: 35 m²/g | Commercial, low viscous correction material[2] |
| Mixed viscosity[9] | 6.4 Pas | 7.1 Pas | 7.3 Pas | 7.3 Pas | 39.8 Pas | 38.9 Pas |
| Thixotropic index of the mixture[8] | 1.1 | 1.1 | 1.1 | 1.1 | 1.1 | 1.7 |
| Processing time[10] | 60 s | 60 s | 60 s | 60 s | 60 s | 60 s |
| End of setting[11] | 230 s | 240 s | 215 s | 215 s | 180 s | 150 s |
| Recovery of shape (ISO 4823) | 99.60% | 99.70% | 99.80% | 99.90% | 99.90% | 99.80% |
| Plasticity and pressure (ISO 4823) | 3.40% | 6.40% | 6.40% | 6.40% | 6.30% | 4.60% |
| Shore A hardness[12] | 51 | 31 | 41 | 41 | 35 | 46 |
| Tear resistance[13] | 170 N/cm² | 40 N/cm² | 225 N/cm² | 225 N/cm² | 174 N/cm² | 200 N/cm² |
| Tear propagation strength[14] | 0.59 N/mm | 0.32 N/mm | 0.59 N/mm | 0.59 N/mm | 2.09 N/mm | 2.09 N/mm |
| Impression result employing the novel impression spoon[15] | Poor sedimentated[4] | Poor too brittle[3] | Excellent | Excellent instable[15] | Good | Poor too thixotropic[9] |
| End of setting, 1 week, 60° C. | 175 s | 280 s | 215 s | 600 s | 180 s | 150 s |
| Mixed viscosity, 1 wee, 60° C. | 7.6 Pas | 7.4 Pas | 7.3 Pas | 6) | 39.8 Pas | 60.2 Pas |
| Thixotropic index, 3 weeks, 60° C. | 1.0 | 1.0 | 1.1 | 6) | 1.1 | 2.6 |

[1] The technical data preventing or limiting the usability of the respective comparative example for the novel impression spoon are marked in bold and italics
[2] Pansil Contact Plus, batch no. 1999, Kettenbach GmbH & Co KG
[3] The cured impression cracks during the removal from the patient's mouth or during the removal from the impression spoon or breaks through
[4] After storage, the properties of the mixed and cured impression material are impaired due to the sedimentation of the single components
[5] When flowing around the teeth, the thixotropically adjusted material causes flow trails in the areas averted from the flow direction which falsify the impression result
[6] The mixed viscosity and the thixotropic index cannot be measured unambiguously due to the excessive delay during crosslinking
[7] The material already cracks during the mounting in the testing apparatus; a meaningful measurement is not possible.
[8] The thixotropic index is the quotient of the viscosity after a measuring time of 25 s and the minimum of viscosity (mixed viscosity)
[9] The mixed viscosity is measured in a RS 150 viscosimeter of the Haake company at 35° C. Oscillation frequency: 1 Hz; plate-plate measuring system; 20 mm cross-serrated; plate distance: 0.25 mm; constant shear stress: 50 Pa for 90 s; subsequently: shear stress ramp; 120 Pa/min; for evaluation, the viscosity value at the minimum of the viscosity curve is used as the mixed viscosity for the table
[10] The given processing time is the time after the beginning of mixing in which the mixed viscosity at 35° C. changes only insignificantly.
[11] The end of setting is measured in a shearing disk oscillometer of the Brabender Company, Cycloviskograph E; oscillation frequency: 4 Hz, gap width: 0.5 mm; cross-serrated plates
[12] The Shore A hardness is measured in a Shore A Durometer of the Zwick Company, model 3100, according to DIN 53504
[13] The tear resistance is measured in a Z010 niversal test apparatus of the Zwick company according to DIN 53515
[14] The tear propagation resistance is measured in a Z010 niversal test apparatus of the Zwick company according to DIN 53515
[15] The impression is performed according to WO-A-97/32536 and WO-A-98/52491
[16] Immediately after the preparation, the impression material has the same positive features as example 27. However, since the employed filler contains water, a decomposition of the platinum catalyst and the SiH crosslinking agent occurs in the storage time which results in a delayed setting. A use in the novel impression spoon is not optimal.

TABLE 3

Viscosities of the mixture of low-viscous impression materials

| Product | Manufacturer | Type | Batch | Mixed viscosity[2] | Thixotropic index[3] | Mixing time[3] | Processing time[4] | End of curing[5] |
|---|---|---|---|---|---|---|---|---|
| Lastic Xtra superfine/Lastic Xtra Flüssigharter | Kettenbach | C silicone | 0299/0499 | 27.3 Pas | [1] | 45 s | 70 s | 430 s |
| Xantopren VL plus/Aktivator universal | Heraeus-Kutzer | C silicone | 090079/100241 | 1100.4 Pas | [1] | 45 s | 0 s | 220 s |
| Panasil Contact Plus | Kettenbach | A silicone | 1999 | 38.9 Pas | 1.7 | 5 s | 60 s | 1506 |
| Provil light CD | Heraeus-Kutzer | A silicone | 120098 | 154.6 Pas | 1.0 | 5 s | 35 s | 160 s |
| Permadyne Tube dünnfließend | Espe | Polyether | RW0057004 | 66.3 Pas | 1.0 | 45 s | 75 s | 440 s |
| Permadyne Garant 2:1 | Espe | Polyether | 29817 | 31.4 Pas | 1.0 | 5 s | 35 s | 427 s |
| Dimension Garant L | Espe | A silicone | 22 | 50.9 Pas | 1.1 | 5 s | 40 s | 280 s |
| Dimension Grarant L Quick | Espe | A silicone | 6 | 449.2 Pas | [1] | 5 s | 35 s | 140 s |
| Aquasil LV | Dentaply | A silicone | 960702 | 79.3 Pas | [1] | 5 s | 25 s | 277 s |
| President light body | Coltene | A silicone | GF092/GE003 | 59.8 Pas | [1] | 5 s | 25 s | 180 s |

[1] The thixotropic index cannot be determined since the thixotropy is superimposed by the beginning setting
[2] The mixed viscosity is measured in a RS 150 viscosimeter of the Haake Company at 35° C.; oscillation frequency: 1 Hz; plate-plate measuring system; 20 mm cross-serrated; plate distance: 0.25 mm; constant shear stress: 50 Pa for 90 s; subsequently: shear stress ramp; 120 Pa/min; for evaluation, the viscosity value at the minimum of the viscosity curve is used as the mixed viscosity for the table
[3] The thixotropic index is the quotient of the viscosity after a measuring time of 25 s and the minimum of viscosity (mixed viscosity)
[4] the given processing time is the time after the beginning of mixing in which the mixed viscosity at 35° C. changes only insignificantly.
[5] The end of setting is measured in a shearing disk oscillometer of the Brabender Company, Cycloviskograph E; oscillation frequency: 4 Hz, gap width: 0.5 mm
[6] Lastic Xtra superfine, Xantopren VL plus, and Permadyne Tube dünnfließend: theses materials are manually mixed on a mixing block by means of a mixing spatula

What is claimed is:

1. An impression material for the use with an impression spoon in a patient, the impression material comprising a curable component and at least one first filler, characterized in that said at least one first filler has a BET surface of 20 to 50 m$^2$/g and is present in amount of 10 to 50% by weight, and the impression material has a thixotropic index $\leq 1.1$ and a viscosity of 1 to 40 Pas.

2. The impression material according to claim 1, characterized in that said at least one first filler has a BET surface of 30 to 40 m$^2$/g and the impression material has a viscosity of 1 to 10 Pas.

3. The impression material according to claim 1, characterized in that, due to the use of the first filler, no polymer separation and filler sedimentation tendencies and no post-stiffening occur during storage life of at least 18 months.

4. The impression material according to claim 1, characterized in that, due to the use of the first filler, tear resistance in the cured state measured according to DIN 53504 is between 150 and 250 N/cm$^2$.

5. The impression material according to claim 1, characterized in that the curable component comprises hydrocolloids, alginates, polyethers, plastics, plasters, condensation-crosslinking silicones, addition-crosslinking silicones, or addition-crosslinking silicone polyethers.

6. The impression material according to claim 2, characterized in that said impression material contains addition-crosslinking silicones and addition-crosslinking silicone polyethers.

7. The impression material according to claim 1, characterized in that said impression material is processable in 20 to 120 s and a curing at the temperature of the mouth (35° C.) occurs within 240 s.

8. The impression material according to claim 1, wherein said first filler is a wet-precipitated silicic acid or a naturally occurring silicic acid having a water content of 2 to 8% by weight.

9. The impression material according to claim 1, wherein said first filler has a density of 2.0 to 2.2 g/cm$^3$, a dibutyl phthalate adsorption according to DIN 53601 between 140 and 180 g/100 g, oil adsorption according to DIN ISO 7875 between 35 and 60 g/100 g, and/or a mean particle size between 0.5 and 20 μm.

10. The impression material according to claim 1, wherein said impression material further comprises at least one second filler having a density between 2.0 and 2.2 g/cm$^3$, a BET surface between 110 and 170 m$^2$/g, and/or a primary particle size between 5 and 30 nm.

11. The impression material according to claim 1, wherein said impression material further comprises a second filler having a density between 2.0 and 2.2 g/cm$^3$, a BET between 130 and 150 m$^2$/g, and/or a primary particle size between 5 and 30 nm.

12. The impression material according to claim 1, wherein said first filler comprises silicon dioxide and metal oxides.

13. The impression material according to claim 1, wherein said first filler comprises silicon dioxide and a metal oxide, wherein the metal oxide is aluminum oxide, calcium oxide, sodium oxide, potassium oxide, iron oxide, or titanium dioxide.

14. The impression material according to claim 1, wherein said first filler comprises silicon dioxide in amounts of from 80 to 100% and metal oxides in amounts of from 0 to 20%.

15. The impression material according to claim 10, wherein said at least one first and/or said at least one second filler is (are) hydrophobized.

16. The impression material according to claim 1, further comprising a second filler existing highly dispersed in the form of hydrophobized silicic acid and the second filler has been prepared by a flame hydrolysis of silicon tetrachloride.

17. The impression material according to claim 1, comprising addition-crosslinking silicones containing components:
   a) unsaturated polysiloxanes, alkenylpolysiloxanes,
   b) organohydrogenpolysiloxanes, and
   c) catalysts.

18. The impression material according to claim 1, comprising addition-crosslinking silicones containing components:
   a) α,ω-unsaturated polysiloxanes, α,ω-alkenylpolysiloxanes,
   b) organohydrogenpolysiloxanes, and
   c) catalysts.

19. The impression material according to claim 1, characterized in that component a) contains α,ω-dialkyl, diaryl, arylalkyl, α,ω-alkenyl, or vinylpolysiloxanes, substituted dialkyl, diaryl, or arylalkyl polysiloxanes or polyethers, or α,ω-vinyl-terminated polydimethylsiloxanes in an amount of 40 to 80% by weight.

20. The impression material according to claim 1, characterized in that component a) contains α,ω-dialkyl, diaryl, arylalkyl, α,ω-alkenyl, or vinylpolysiloxanes, substituted dialkyl, diaryl, or arylalkyl polysiloxanes or polyethers, or α,ω-vinyl-terminated polydimethylsiloxanes in an amount of 50 to 70% by weight.

21. The impression material according to claim 1, characterized in that component b) contains alkyl or arylorganohydrogenpolysiloxanes.

22. The impression material according to claim 17, characterized in that component b) contains polyhydrogenpolydimethylsiloxanes having at least 2 SiH groups or an SiH content of from 0.1 to 15 mmol/g in an amount of 2 to 40% by weight.

23. The impression material according to claim 17, characterized in that component b) contains polyhydrogenpolydimetbylsiloxanes having at least 2 SiH groups or an SiH content of from 0.1 to 15 mmol/g in an amount of 10 to 30% by weight.

24. The impression material according to claim 17, characterized in that component c) contains catalysts of transition metals of the $8^{th}$ side group of the periodic system in a percentage range of 0.0001 to 0.1% by weight based on the pure metal.

25. The impression material according to claim 17, characterized in component c) contains catalysts, salts, or forms of transition metals of the $8^{th}$ side group of the periodic system existing as complexes or colloids in a percentage range of 0.0001 to 0.1% by weight based on the pure metal.

26. The impression material according to claim 17, characterized in that component c) contains hydrosilylation catalysts, salts, or forms of platinum, palladium, or rhodium existing as complexes or colloids in a percentage range of 0.0001 to 0.1% by weight based on the pure metal.

27. The impression material according to claim 17, characterized in that component c) contains platinum complexes prepared from hexachloroplatinic acid or from platinum salts (Karstedt catalysts) in a percentage range of 0.0001 to 0.1% by weight based on the pure metal.

28. The impression material according to claim 27, characterized in that the percentage range is 0.0005 to 0.1% by weight based on the pure metal.

29. The impression material according to claim 1, wherein said first filler is present in an amount range of 20 to 30% by weight.

30. The impression material according to claim 1, comprising polysiloxanes having methacrylate groups and an initiator system activatable by light.

31. The impression material according to claim 1, comprising polysiloxanes having methacrylate groups and an initiator system activatable by UV light.

32. The impression material according to claim 17, characterized in that ingredients a) and c) exist in a spatially separated manner.

33. The impression material according to claim 1, characterized in that said first filler is inorganic and the impression material further comprises a second filter, the second filler being an inorganic, reinforcing filler hang a BET surface greater than the BET surface of the first filler.

34. The impression material according to claim 33, wherein the second filler has a BET surface of from 50 to 700 $m^2$/g.

35. The impression material according to claim 33, wherein the second filler has a BET surface of from 110 to 170 $m^2$/g.

36. The impression material according to claim 33, wherein said first filler is a wet-precipitated silicic acid or a naturally occurring silicic acid having a water content of 2 to 8% by weight.

37. The impression material according to claim 33, wherein said first filler has a density of 2.0 to 2.2 g/$cm^3$, a dibutyl phthalate adsorption according to DIN 53601 between 140 and 180 g/100 g, an oil adsorption according to DIN ISO 7875 between 35 and 60 g/100 g and/or a mean particle size between 0.5 and 20 μm.

38. The impression material according to clam 33, wherein the second filler is hydrophobized.

\* \* \* \* \*